United States Patent
Foong et al.

(10) Patent No.: US 10,405,775 B2
(45) Date of Patent: Sep. 10, 2019

(54) APPARATUS AND METHOD FOR TRACKING A DEVICE

(71) Applicants: Singapore University of Technology and Design, Singapore (SG); National University of Singapore, Singapore (SG)

(72) Inventors: Shaohui Foong, Singapore (SG); Zhenglong Sun, Singapore (SG); U-Xuan Tan, Singapore (SG); Tee Hui Teo, Singapore (SG); Asim Shabbir, Singapore (SG)

(73) Assignee: Singapore University of Technology and Design & National University of Singapore, Singapore (SG)

( * ) Notice: Subject to any disclaimer, the term of this patent is extended or adjusted under 35 U.S.C. 154(b) by 617 days.

(21) Appl. No.: 15/038,412

(22) PCT Filed: Nov. 21, 2014

(86) PCT No.: PCT/SG2014/000552
§ 371 (c)(1),
(2) Date: May 20, 2016

(87) PCT Pub. No.: WO2015/076756
PCT Pub. Date: May 28, 2015

(65) Prior Publication Data
US 2016/0287134 A1    Oct. 6, 2016

(30) Foreign Application Priority Data
Nov. 21, 2013    (SG) .................................. 201308736

(51) Int. Cl.
*A61B 5/06*    (2006.01)
*A61B 5/00*    (2006.01)
(Continued)

(52) U.S. Cl.
CPC .............. *A61B 5/062* (2013.01); *A61B 5/061* (2013.01); *A61B 5/6805* (2013.01); *A61B 5/742* (2013.01);
(Continued)

(58) Field of Classification Search
CPC ....... A61B 5/062; A61B 5/742; A61B 5/6805; A61B 5/061; A61B 5/746; A61B 34/20;
(Continued)

(56) References Cited

U.S. PATENT DOCUMENTS

2005/0043634 A1\* 2/2005 Yokoi ................ A61B 1/00016
600/476
2005/0143643 A1\* 6/2005 Mimai ............... A61B 1/00016
600/407
(Continued)

FOREIGN PATENT DOCUMENTS

| JP | 03000078 | 1/1991 |
|---|---|---|
| JP | 6285043 | 10/1994 |
| WO | WO2015076756 A1 | 5/2015 |

OTHER PUBLICATIONS

Foreign Communication from a Related Counterpart—International Search Report and Written Opinion, dated Feb. 17, 2015, PCT/SG2014/000552, filed on Nov. 21, 2014.
(Continued)

*Primary Examiner* — Bo Jospeh Peng

(57) ABSTRACT

The present invention relates to an apparatus for tracking a device comprising a magnet as the device is inserted through a subject. The apparatus is wearable by the subject and comprises a unit configured to conform to the subject. The apparatus further comprises magnetic sensors arranged with the unit. In use, the magnetic sensors detect magnetic fields of the magnet and the detected magnetic fields are processed
(Continued)

to determine a position of the magnet. This allows tracking of the device as the device is inserted through the subject.

9 Claims, 5 Drawing Sheets

(51) Int. Cl.
    *A61B 34/20*     (2016.01)
    *A61J 15/00*     (2006.01)
    *A61B 90/00*     (2016.01)
    *A61M 25/01*     (2006.01)

(52) U.S. Cl.
    CPC ........... *A61B 34/20* (2016.02); *A61J 15/0088* (2015.05); *A61B 5/746* (2013.01); *A61B 2034/2051* (2016.02); *A61B 2090/3954* (2016.02); *A61J 15/0003* (2013.01); *A61M 25/0127* (2013.01)

(58) Field of Classification Search
    CPC ..... A61B 2034/2051; A61B 2090/3954; A61J 15/0088; A61J 15/0003; A61M 25/0127
    See application file for complete search history.

(56) References Cited

U.S. PATENT DOCUMENTS

2007/0123772 A1*   5/2007   Euliano ................. A61B 5/073
                                                                                     600/407
2007/0167743 A1     7/2007   Honda et al.
2007/0282169 A1    12/2007   Tsujita

OTHER PUBLICATIONS

Foreign Communication from a Related Counterpart—International Preliminary Report on Patentability, dated Dec. 22, 2015, PCT/SG2014/000552, filed on Nov. 21, 2014.

* cited by examiner (a)

(b)

APPARATUS AND METHOD FOR TRACKING A DEVICE

CROSS-REFERENCE TO RELATED APPLICATIONS

The present application is a filing under 35 U.S.C. 371 as the National Stage of International Application No. PCT/SG2014/000552, filed Nov. 21, 2014, entitled "AN APPARATUS AND METHOD FOR TRACKING A DEVICE," which claims the benefit of and priority to Singapore Application No. 201308736-6, filed with the Intellectual Property Office of Singapore on Nov. 21, 2013, both of which are incorporated herein by reference in their entirety for all purposes.

FIELD OF THE INVENTION

The present invention relates to an apparatus and method for tracking a device comprising a magnet, and a kit comprising the apparatus and the device.

BACKGROUND OF THE INVENTION

Nasogastric (NG) intubation refers to the insertion of a plastic tube through the nose, past the throat and down into the stomach of a subject. NG intubation is a vital medical procedure and a common clinical procedure for both diagnostic and therapeutic purposes.

NG intubation is commonly performed "blindly" i.e. without any visual aid or indication. This places reliance on the user's skill and experience, and can lead to an erroneous insertion and misplacement of the NG tube. Studies have shown that these errors can result in a whole spectrum of thoracic and non-thoracic complications. For example, insertion of the NG tube into the subject's airways, or coiling or knotting of the NG tube during the insertion process, can cause complications, perforation and sometimes, even fatality.

To date, different bedside methods of localizing a NG tube within a subject have been developed. In particular, radiography is considered the gold standard for this purpose. However, it is not desirable to use radiography each time the NG tube needs to be inserted. Further, for long-term enteral feeding, the position of the tip of the tube is preferably determined prior to initiation of the tube feeding (which may be required at least three times a day). It is again not desirable to use radiography each time before tube feeding. This is because of the expenses involved in using radiography and the radiation exposure (which is especially an issue of concern when the subject is a child). Further, there may be regions where X-ray machines are not available.

SUMMARY OF THE INVENTION

The present invention aims to provide a new and useful apparatus and method for tracking a device comprising a magnet when the device is inserted through a subject.

In general terms, the present invention proposes an apparatus wearable by the subject and conformable to the subject, with the apparatus comprising magnetic sensors configured to detect magnetic fields of the magnet, so as to track the device.

Specifically, a first aspect of the present invention is an apparatus for tracking a device comprising a magnet, the apparatus being wearable by a subject and comprising: a unit configured to conform to the subject; and magnetic sensors arranged with the unit to detect magnetic fields of the magnet as the device is inserted through the subject; wherein the detected magnetic fields are processable to determine a position of the magnet to track the device as the device is inserted through the subject.

The first aspect of the present invention facilitates the tracking of the device within the subject. To begin the tracking process, the subject simply wears the apparatus. Since the unit is configured to conform to the subject, the apparatus can be worn by the subject comfortably and the magnetic sensors can be closer to the subject to improve the accuracy of the device tracking.

The unit may comprise at least one flexible element configured to conform to the subject. For example, the unit may comprise rigid parts interspersed with deformable parts. Having rigid parts interspersed with the deformable parts increases the ease of deployment and comfort for the subject. Such a unit is also easily stored and sufficiently flexible to adapt to different subjects, allowing the unit to better conform to each subject, thereby helping to increase the accuracy of the device tracking.

The unit may be bendable to conform to the subject and the apparatus may further comprise flex sensors arranged with the unit and configured to determine an extent the unit bends. These flex sensors help to determine the spatial distribution of the magnetic sensors which is useful in determining the position of the magnet as the device is inserted through the subject. For example, the extent the unit bends may be used to determine positions of the magnetic sensors when the unit is bent and the position of the magnet may be determined using the detected magnetic fields and the positions of the magnetic sensors when the unit is bent.

The unit may comprise: a first portion configured to ensure that the device is inserted into a target part of the subject; and a second portion configured to ensure that the device is inserted through the subject to a target destination in a desired manner. Having multiple portions allow these portions to be configured differently. For instance, the portion to be worn around a more important area of the subject can be configured to have a higher tracking accuracy (by for example, having more magnetic sensors) whereas to save cost, the portion to be worn around a less important area of the subject can be configured to have a lower tracking accuracy (by for example, having less magnetic sensors).

The apparatus may further comprise processing means configured to process the detected magnetic fields to determine the position of the magnet. This removes the need for external processing means.

The apparatus may further comprise indicating means configured to indicate if the device is inserted through the subject in a desired manner. For example, the indicating means may comprise a plurality of indication elements located in positions corresponding to respective points along a particular part of the subject and wherein each indication element is configured to provide an indication when the magnet is within a predetermined range of the corresponding point along the particular part of the subject. This allows the user to track the insertion of the device along the particular part of the subject using the indication elements.

Preferably, the detected magnetic fields are also processable to determine an orientation of the magnet. This allows the user to know if the device is knotted or coiled.

A second aspect of the present invention is a method for tracking a device comprising a magnet, the method comprising: a subject wearing the apparatus in accordance with the first aspect, with the unit conforming to the subject; detecting magnetic fields of the magnet with the magnetic sensors as the device is inserted through the subject; and processing the detected magnetic fields to determine the position of the magnet to track the device as the device is inserted through the subject.

Processing the detected magnetic fields may comprise: inputting the detected magnetic fields into a trained artificial neural network model to determine the position of the magnet. Using a trained artificial neural network to determine the position of the magnet increases the accuracy of this determination.

A third aspect of the present invention is a kit comprising: a device comprising a magnet; and an apparatus according to the first aspect.

The device in the first, second or third aspect may be a NG tube or other medical device, and the subject may be a person. Alternatively, the device may be a non-medical device (e.g. an industrial device such as a rotor) and the subject may be an object (e.g. an industrial element such as a motor).

BRIEF DESCRIPTION OF THE FIGURES

Embodiments of the invention will now be described, for the sake of example only, with reference to the following drawings in which.

DETAILED DESCRIPTION OF THE EMBODIMENTS

Figure 1:
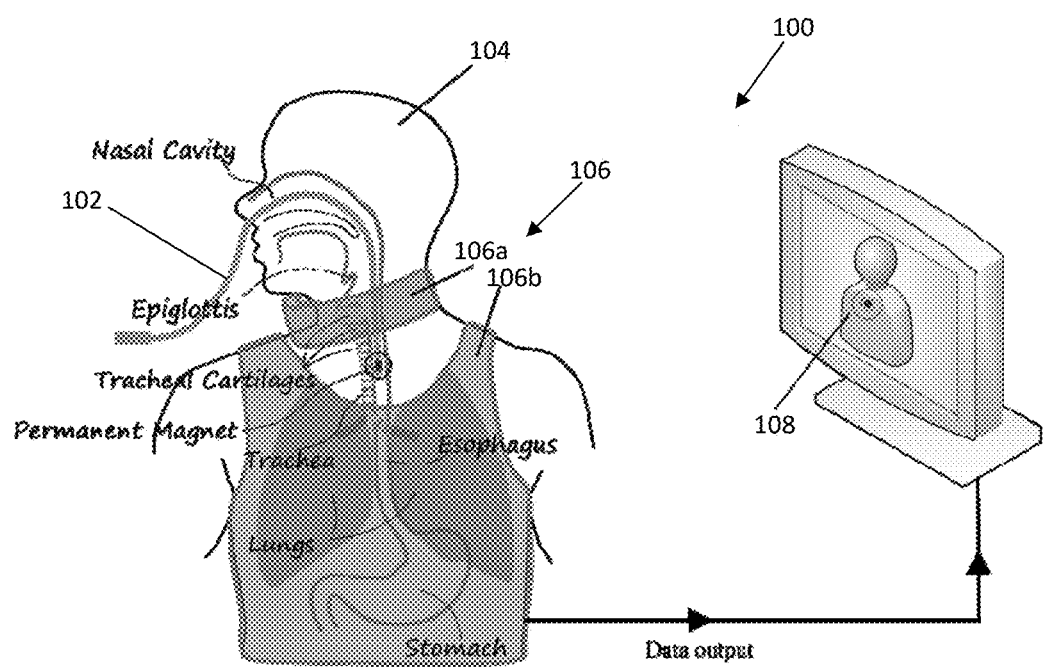
FIG. 1 shows a system for tracking an insertion of a device through a subject according to an embodiment of the present invention.

FIG. 1 shows a system 100 for tracking an insertion of a device in the form of a NG tube 102 through a subject 104 according to an embodiment of the present invention. This system 100 allows for real-time tracking of the NG tube 102 within the subject 104. The system 100 comprises a permanent magnet (PM) embedded at the tip of the NG tube 102 and an apparatus 106 for tracking the NG tube 102 comprising the PM. A visualizer (or visual display/indicator) 108 in the form of a computer monitor is also included in the system 100. This visualizer 108 is connected to the apparatus 106 and is configured to show the real-time location of the NG tube 102 based on the tracking by the apparatus 106. The visualizer 108 allows the clinician to monitor the insertion of the NG tube 102 through a real-time updated physiology display.

The apparatus 106 is wearable by the subject 104 and comprises magnetic sensors. Hence, the apparatus 106 may also be referred to as a wearable sensor network 106. In particular, the wearable sensor network 106 comprises a unit having flexible elements configured to conform to the subject 104. In this embodiment, the unit is configured to wrap around target areas including the torso, neck and stomach of the subject 104. The magnetic sensors of the wearable sensor network 106 are embedded with the unit to detect magnetic fields of the magnet as the NG tube 102 is inserted through the subject 104. These magnetic fields are processable to determine a position and an orientation of the magnet, allowing the NG tube 102 to be tracked.

The wearable sensor network 106 also comprises processing means in the form of FPGA localization electronics integrated with the unit. The FPGA localization electronics are configured to process the magnetic fields detected by the magnetic sensors to determine the position and orientation of the magnet.

The unit of the wearable sensor network 106 comprises a first portion configured to ensure that the NG tube 102 is inserted into a target part of the subject 104 and a second portion configured to ensure that the NG tube 102 is inserted through the subject 104 to a target destination of the subject 104 in a desired manner.

In particular, in the embodiment of FIG. 1, the first portion comprises a neck attachment 106a to be worn around the subject's 104 neck. The neck attachment 106a is configured to ensure that the NG tube 102 is inserted into the esophagus of the subject 104 and not misplaced into another part of the subject 104 (for example, through the subject's 104 airways into the subject's 104 trachea which can cause serious complications or even fatality). The second portion comprises a body attachment 106b to be worn over the body of the subject 104. The body attachment 106b is configured to track the NG tube 102 through a part of the subject 104 to the subject's 104 stomach. This tracking is done after the insertion of the NG tube 102 into the esophagus is confirmed using the neck attachment 106a. As shown in FIG. 1, in this embodiment, there is a gap between the neck attachment 106a and the body attachment 106b, and the path of the NG tube 102 through the part of the subject 104 corresponding to this gap is not tracked. However, it is not necessary to have this gap and in other embodiments, this gap can be smaller or can be removed altogether. Alternatively, this gap may also be bigger.

Figure 2:
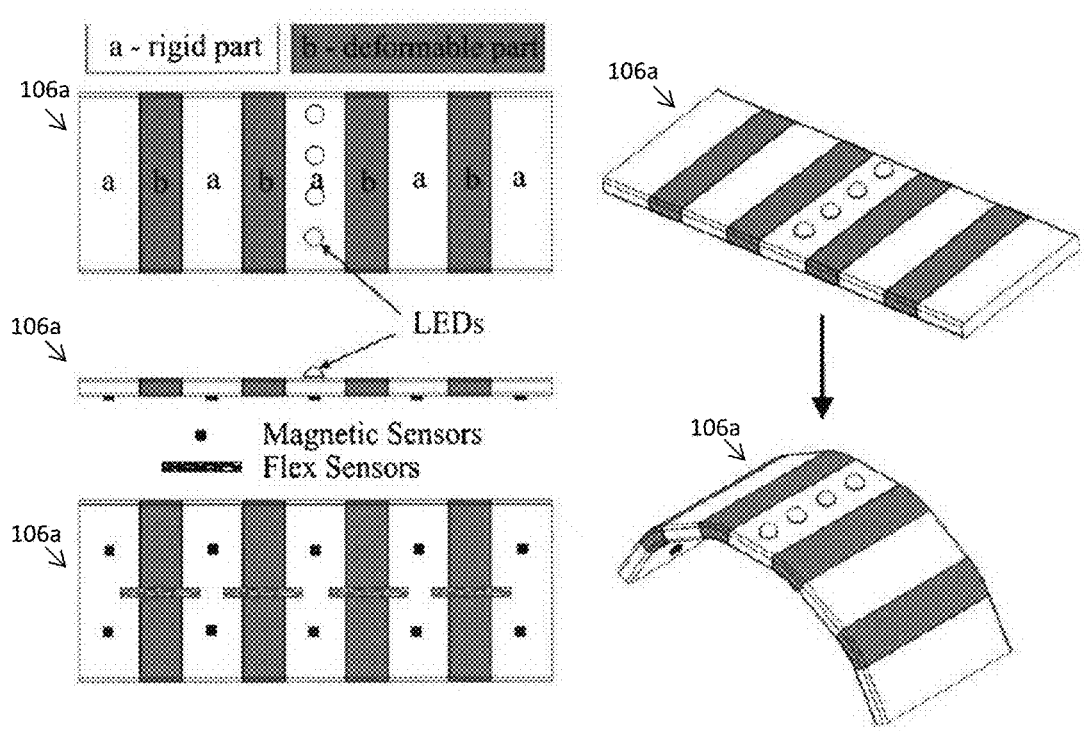
FIG. 2 shows a neck attachment of an apparatus of the system of FIG. 1.

FIG. 2 shows the neck attachment 106a of the wearable sensor network 106. The neck attachment 106a comprises five rigid rectangular parts (labeled as "a") interspersed with four deformable rectangular parts (labeled as "b"). Having rigid parts interspersed with the deformable parts increases the ease of deployment and comfort for the subject 104 when the neck attachment 106a is worn around the neck of the subject 104. Such a neck attachment 106a is also easily stored and sufficiently flexible to adapt to different neck circumferences of different subjects. Thus, the neck attachment 106a can conform to the subject's 104 neck and this can help bring the magnetic sensors closer to the subject 104, increasing the accuracy of the magnetic field detection.

As shown in FIG. 2, the neck attachment 106a comprises magnetic sensors pre-integrated into it. More specifically, two magnetic sensors (shown as black squares in FIG. 2) are embedded on a first surface of each rigid part "a". The magnetic sensors are located along the length of the rigid part "a" with each magnetic sensor positioned approximately in the middle of each half of the rigid part "a". Further, one flex sensor (shown as a shaded rectangle in FIG. 2) is embedded on a surface of and across the breadth of each deformable part "b". The flex sensors are approximately in the middle of the lengths of the deformable parts "b". The magnetic sensors and flex sensors are embedded on the same side of the neck attachment 106a. Each flex sensor on a deformable part "b" is arranged to contact the adjacent rigid parts "a" and is configured such that when the deformable part "b" is bent, the flex sensor bends accordingly. Because of the arrangement of the rigid and deformable parts, the neck attachment 106a is bendable to wrap around the subject's 104 neck. The flex sensors are configured to determine an extent the neck attachment 106a bends when the neck attachment 106a is deformed to fit the particular subject 104. This helps to determine the spatial distribution of the magnetic sensors, thereby allowing the positions of the magnetic sensors to be determined. In particular, bending (i.e. deformation) of the neck attachment 106a can be modeled analytically using a beam deformation model since the required parameters of the neck attachment 106a are known. The deformation of the neck attachment 106a as determined by the flex sensors readings in tandem with the beam deformation model can be used to obtain the positions of the magnetic sensors when the neck attachment 106a is deformed. These positions of the magnetic sensors can be used together with the detected magnetic fields for the localization algorithm. This helps to increase the accuracy of the NG tube 102 localization since the magnetic sensors positions can be determined more accurately with the use of the flex sensors.

Indicating means in the form of four bi-colored LEDs are embedded on the rigid part "a" in the middle of the neck attachment 106a. These LEDs serve to indicate if the NG tube 102 is inserted through the subject 104 in a desired manner. As shown in FIG. 2, the LEDs are embedded on the surface opposite the surface on which the magnetic sensors are. The LEDs are positioned equidistant from each other along the length of the rigid part "a". Further, the LEDs are connected to the processing means and are configured to indicate the position of the tip of the NG tube 102 (where the PM is) based on the output from the processing means. In particular, the LEDs are located in positions corresponding to respective points along the esophagus of the subject 104. Each LED is configured to display a green light as the tip of the NG tube 102 reaches a predetermined range of the corresponding point along the esophagus. This predetermined range may depend on the spacing between two adjacent LEDs and may be for example 1 cm. This range may be referred to as the range of the LED. Each LED may be configured to display a green light when the tip of the NG tube 102 reaches a predetermined distance before the corresponding point along the esophagus or only when the tip of the NG tube 102 reaches a predetermined distance beyond the corresponding point along the esophagus (or in other words, underneath this corresponding point). This helps the clinician track how far into the esophagus the NG tube 102 has been inserted. The LEDs are further configured such that if output from the processing means indicate that the tip of the NG tube 102 is being inserted into an undesirable part of the subject 104, all the LEDs will display a blinking red light simultaneously. Therefore, the LEDs not only help to indicate the position of the NG tube's 102 tip, they also serve as an alarm to the occurrence of any anomalies. Based on these LEDs, the clinician is able to know if the NG tube 102 is being inserted correctly.

Figure 3:
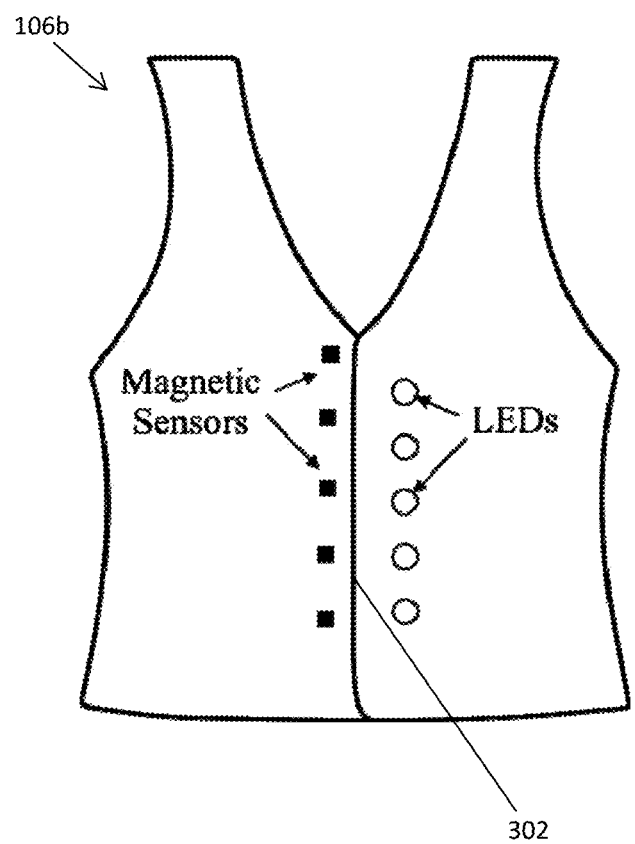
FIG. 3 shows a body attachment of an apparatus of the system of FIG. 1.

FIG. 3 shows the body attachment 106b of the wearable sensor network 106. The body attachment 106b is formed of flexible fabric and is designed to ensure that the NG tube 102 insertion is not obstructed and that the NG tube 102 does not coil in the process of its insertion through the subject 104. The body attachment 106b is also used to confirm the final placement of the NG tube 102 in the stomach.

As shown in FIG. 3, the body attachment 106b is in the form of a vest openable wholly along the line 302 at its front. The body attachment 106b comprises five magnetic sensors and indicating means in the form of five bi-coloured LEDs. The LEDs of the body attachment 106b are arranged a distance from the line 302 and in an approximately straight line parallel to the line 302. The magnetic sensors are also arranged a distance from the line 302 and in an approximately straight line parallel to the line 302 but the LEDs and magnetic sensors are arranged on different sides of the line 302. The LEDs and magnetic sensors are also arranged on opposite surfaces of the body attachment 106b such that when the subject 104 wears the body attachment 106b, the magnetic sensors on the internal surface abut the subject 104 whereas the LEDs on the external surface can be seen by the clinician.

Similar to the LEDs of the neck attachment 106a, the LEDs of the body attachment 106b serve to indicate if the NG tube 102 is inserted through the subject 104 in a desired manner. The LEDs of the body attachment 106b are located in positions corresponding to respective points along the body of the subject 104. Each LED is configured to display a green light as the tip of the NG tube 102 reaches a predetermined range of the corresponding point along the body. Similarly, this predetermined range may depend on the spacing between two adjacent LEDs and may be for example 1 cm. Each LED may be configured to display a green light when the tip of the NG tube 102 reaches a predetermined distance before the corresponding point along the esophagus or only when the tip of the NG tube 102 reaches a predetermined distance beyond the corresponding point along the body (or in other words, underneath this corresponding point). The LEDs are further configured such that if output from the processing means indicate that the tip of the NG tube 102 is being inserted into an undesirable part of the subject 104, all the LEDs will display a blinking red light simultaneously.

In use, the system 100 is first set up. In particular, the subject 104 wears the wearable sensor network 106 with the unit conforming to the subject 104. This is done by placing the body attachment 106b over the subject's 104 body with the magnetic sensors abutting the body and with the flexible fabric conforming to the body, and by placing the neck attachment 106a around the subject's 104 neck with the magnetic sensors abutting the neck and with the deformable parts conforming to the subject's 104 neck. The wearable sensor network 106 is then connected to the visualizer 108. The set up process also includes embedding the PM at the tip of the NG tube 102 (if the NG tube 102 does not already comprise such a PM).

After setting up the system 100, the tip of the NG tube 102 comprising the PM is inserted through the subject's 104 nostril, nasal passage, pharynx towards the esophagus. Then, the insertion of the tip of the NG tube 102 into the esophagus is tracked using the magnetic sensors embedded on the neck attachment 106a. When the tip of the NG tube 102 enters the esophagus and reaches within the range of the LED at the top of the neck attachment 106a, this LED displays a green light. As the tip of the NG tube 102 further enters the esophagus, the remaining LEDs sequentially display green lights (from the topmost LED to the bottommost LED). Occasionally, a green light may not appear and instead the LEDs start displaying a blinking red light simultaneously. This indicates that the tip of the NG tube 102 is being inserted into an undesirable part of the subject 104 and in such circumstances, the clinician may take corrective measures to adjust the path of the NG tube 102.

Having all the LEDs display a green light indicates that the tip of the NG tube 102 is successfully inserted into the esophagus. In this embodiment, the LEDs of the neck attachment 106a are arranged such that when the tip of the NG tube 102 is inserted 5 cm into the esophagus, all the LEDs display a green light indicating that the tip of the NG tube 102 is successfully inserted into the esophagus. The tip of the NG tube 102 is then further inserted through the subject 104 to the target destination which is the subject's 104 stomach. This further insertion is tracked using the magnetic sensors embedded on the body attachment 106b. Similarly, when the tip of the NG tube 102 reaches within the range of the LED at the top of the body attachment 106b, this LED displays a green light. As the tip of the NG tube 102 further enters the subject 104 towards the subject's 104 stomach, the remaining LEDs sequentially display green lights (from the topmost LED to the bottommost LED). Occasionally, a green light may not appear and instead the LEDs of the body attachment 106b start displaying a blinking red light simultaneously. This indicates that the tip of the NG tube 102 is being inserted into an undesirable part of the subject 104 and in such circumstances, the clinician may take corrective measures to adjust the path of the NG tube 102.

Determination of the position/orientation of the NG tube 102 tip is achieved by detecting and processing the static magnetic fields of the embedded magnet at the tip of the NG tube 102. Since this magnet is permanent, its static magnetic fields are fixed and thus, can be calibrated and modeled using an artificial neural network (ANN) field modeling approach as described in PCT/SG2014/000200, the contents of which are herein incorporated by reference. Utilizing this accurate and computationally inexpensive model, the spatial information of the tip of the NG tube 102 can be obtained in real time using the wearable sensor network 106. The principle of magnetic-based localization used in the system 100 is shown in FIG. 4.

In particular, a set of axes i.e. X axis, Y axis and Z axis respectively corresponding to the frontal axis, longitudinal axis and sagittal axis of the subject 104 are defined. The intersection of these axes is set as the origin $[0,0,0]^T$.

Figure 4:
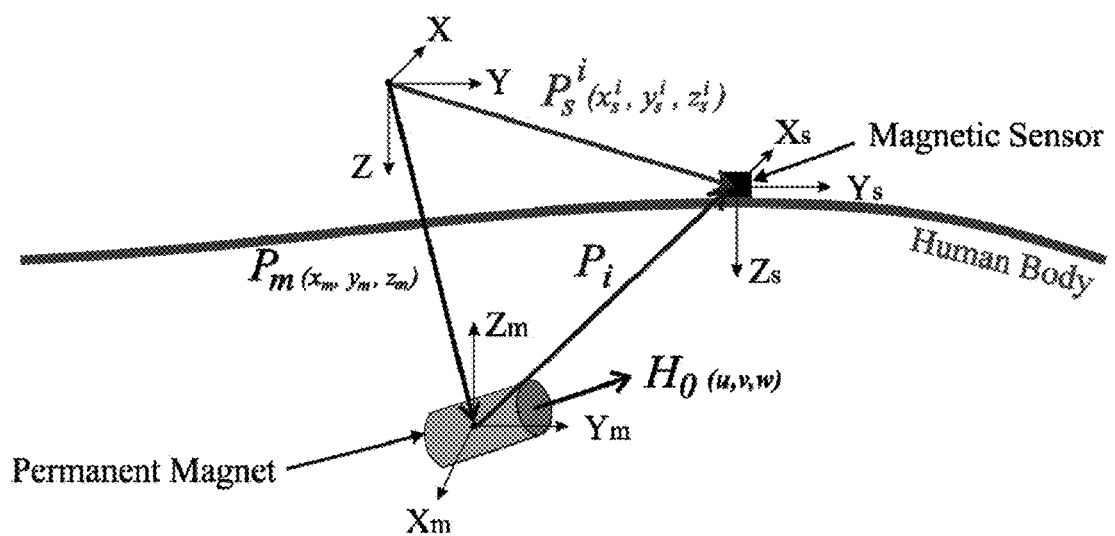
FIG. 4 shows the principle of magnetic-based localization used in the system of FIG. 1.

As shown in FIG. 4, the magnet source is represented at the center of the permanent magnet i.e. position of the permanent magnet is $P_m=[x_m, y_m, z_m]^T$. The orientation of the dipole in alignment with the magnetization axis of the PM is defined as a unit vector $H_0=[u, v, w]^T$, whereby $$u^2+v^2+w^2=1 \quad (1)$$

The readings from a total of m flex sensors can be represented as $FS=[fs_1, fs_2, \ldots, fs_m]^T$. Based on the flex sensors readings, the deformation of the neck or body attachment 106a, 106b can be determined via a beam deformation model. Using this deformation of the neck or body attachment 106a, 106b, the position of the $i^{th}$ sensor in the wearable sensor network 106 (embedded on either the neck attachment 106a or the body attachment 106b) $P_s^i=[x_s^i, y_s^i, z_s^i]^T$ can be determined via a geometrical model.

The magnetic field detected by the $i^{th}$ sensor can be represented as $B_{measured}(P_s^i)$. Using a nonlinear optimization algorithm, a cost function can be defined as shown in Equation (2) and minimized to determine the position $P_m=[x_m, y_m, z_m]^T$ and orientation $H_0=[u, v, w]^T$ of the permanent magnet. In Equation (2), n is the number of magnetic sensors used for determining the position and orientation of the magnet. n need not be the total number of magnetic sensors embedded in both the neck attachment 106a and the body attachment 106b. For example, if a particular LED is emitting a green light, it may be possible to use only the magnetic sensors around this LED and the next LED for determining the position $P_m=[x_m, y_m, z_m]^T$ and orientation $H_0=[u, v, w]^T$ of the magnet. Generally, all the sensors of the neck attachment 106a are used for determining the position and orientation of the magnet as the NG tube 102 is inserted into the subject's esophagus, whereas for the body attachment 106b, since it is unlikely for the magnetic fields of the PM to be detected by sensors far away from the PM, not all the sensors of the body attachment 106b are used as the NG tube 102 is inserted towards the subject's stomach. However, this is not necessary and the number of sensors to be used for either the neck attachment 106a or the body attachment 106b may be varied.

$$C = \sum_{i=1}^{n} \|B_{model}(P_s^i) - B_{measured}(P_s^i)\|^2 \quad (2)$$

In the above embodiment, the ANN model is used to describe the magnetic fields of the permanent magnet.

In particular, an ANN is first trained to estimate the magnetic fields induced by one specific magnet which will later be used as the permanent magnet embedded in the tip of the NG tube 102. The training of the ANN involves using an automated platform, such as a magnetic field mapping system or an industrial robot, to move the specific magnet to a series of randomly chosen positions and orientations relative to a magnetic sensor fixed at a particular position. Magnetic field measurements by the magnetic sensor when the specific magnet is moved to the different positions and orientations are obtained.

For the ANN training, the inputs to the ANN are the positions and orientations of the specific magnet $I=[x_m, y_m, z_m, u, v, w]^T$ and the outputs of the ANN are the modeled magnetic field measurements $O=B_{ANN}=[B_x, B_y, B_z]$ when the specific magnet is at the positions and orientations. For example, a two-layers ANN can be mathematically represented as shown in Equation (3).

$$O(k) = g\left(\sum_{j=0}^{M} w_{kj}^{(2)} g\left(\sum_{i=0}^{d} w_{ij}^{(1)} I(i)\right)\right) \quad (3)$$

where $g(\circ)$ is the activation function, w is the weight function, $I(i)$ is the $i^{th}$ input of I and $O(k)$ is the $k^{th}$ output of O. The number in parenthesis in Equation (3) signifies the layer in the ANN architecture. During the training process, the weight function w is determined by minimizing the differences between the modeled magnetic field measurements $O=B_{ANN}=[B_x, B_y, B_z]$ calculated using Equation (3) and the actual magnetic field measurements obtained when the specific magnet is moved to the different positions and orientations. During training, it is preferable to move the specific magnet to as many positions and orientations as practically possible (with these positions and orientations being within the range of positions and orientations that the PM will be moved to during the actual use of the apparatus 106). This can help increase the accuracy of the trained ANN model.

After the training process, Equation (3) is used to obtain modeled magnetic field measurements. These modeled magnetic field measurements are then used as $B_{model}(P_s^i)$ in Equation (2) to determine the location $P_m=[x_m, y_m, z_m]^T$ and orientation $H_0=[u, v, w]^T$ of the permanent magnet (which is the specific magnet used during the training) embedded in the tip of the NG tube 102 as the NG tube 102 is inserted through a subject 104. Thus, the location of the tip of the NG tube 102 can be tracked.

Further, calibration of the system 100 is performed prior to each use. In this embodiment, the calibration is performed as follows. Once the system 100 is powered on, all the magnetic sensors are reset such that their readings reflecting the magnetic fields they detect become zero. This helps to remove influences due to the ambient environment so that any changes in the magnetic field measurements are due to movement of the permanent magnet embedded in the NG tube 102.

Various modifications will be apparent to those skilled in the art.

For example, although in the embodiment shown in FIG. 1, the system 100 is used for the insertion of a NG tube 102 into a subject 104, the same system 100 can be modified in a manner for localization purposes in other medical applications (such as for surgical catheter tracking, other medical instrument/device insertion or for locating automated robotic devices in a subject's body). The system 100 may also be used for non-medical applications such as for industrial automation and control when devices have to be localized within a confined space. For example, the system 100 can be used to determine a position or orientation of a rotor inside a motor.

Further, the apparatus 106 need not comprise the processing means. Instead, external processing means may be connected to the magnetic sensors of the apparatus 106 to process the detected magnetic fields. The apparatus 106 also need not comprise the indicating means. Again, external indicating means may be used instead. Alternatively, a clinician may simply rely on the visualizer 108 to monitor the insertion of the device and the system need not comprise any indicating means. Similarly, the system need not comprise the visualizer and the clinician may simply rely on the indicating means. However, it is preferable if both the visualizer and indicating means are present in the system 100. The visualizer also need not be a computer monitor but can instead be a different type of display such as a mobile device. The indicating means also need not comprise LEDs but can instead comprise other types of indication elements (such as alarms) as long as they can provide some form of indication. In one example, the indicating means comprise alarms and if output from the processing means indicate that the tip of the NG tube 102 is being inserted into an undesirable part of the subject 104, all the alarms will output a sound simultaneously.

Different types of magnets may be used as the PM. However, the magnet is preferably small, cylindrical and hermetically embedded in the device e.g. the NG tube 102. This will allow the magnet to operate passively i.e. it does not require any power source. With this, it is also not necessary to change the appearance and functionality of the device and therefore, the clinician can continue using existing intubation procedures. Similarly, different types of magnetic sensors may be used. However, it is preferable if the magnetic sensors can be easily replaced.

Figure 5:
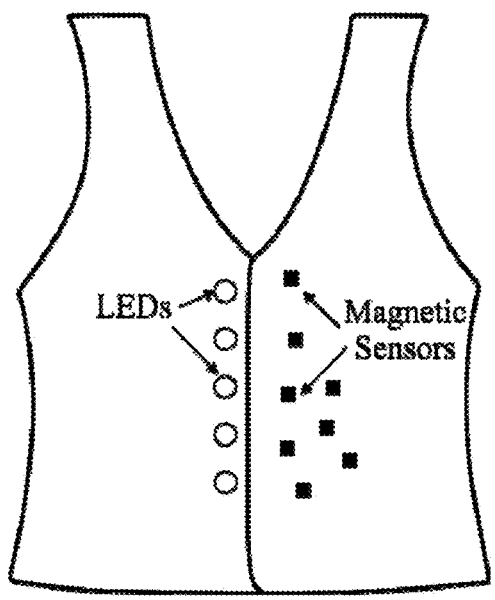
FIG. 5(a) shows an alternative to the body attachment of FIG. 3
FIG. 5(b) shows a subject wearing the alternative of FIG. 5(a).
Figure 5:
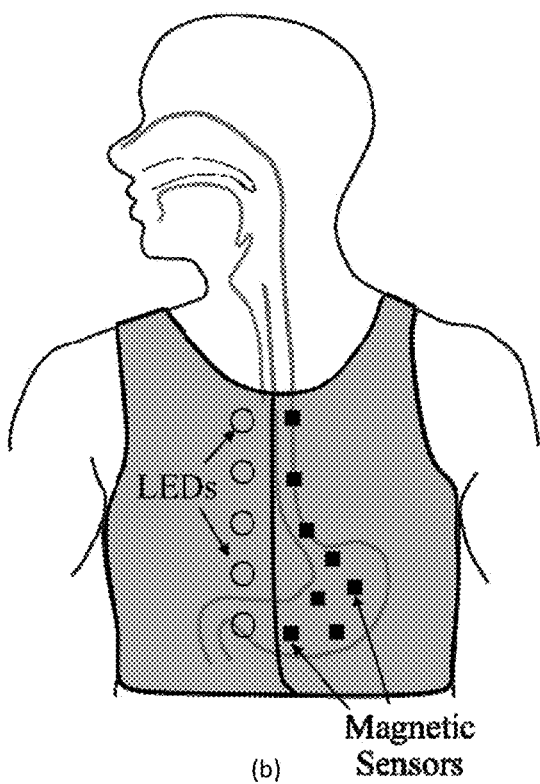

Also, the configuration of the apparatus 106 need not be identical to that described above. For example, there may be more rigid and/or deformable parts, there need not be two portions, and the LEDs and magnetic sensors may be placed in a different manner. It is sufficient as long as the apparatus 106 is wearable by a subject and is conformable to the subject. For example, FIG. 5(a) shows an alternative body attachment with the magnetic sensors placed in a different manner from that in the above embodiment and FIG. 5(b) shows a subject wearing this alternative body attachment. In particular, as shown in FIG. 5(b), when the subject wears this alternative body attachment, the magnetic sensors are located on the left side of the subject's body and are at positions corresponding to points distributed along the subject's esophagus and stomach.

The length of the neck attachment 106a can be varied. For example, the neck attachment 106a can have a length that allows it to go around the entire neck of a typical adult or a shorter length. It is sufficient as long as the neck attachment 106a has a length long enough to allow the placement of sufficient sensors around the subject's 104 throat to obtain a certain level of tracking accuracy that is high enough. Typically, for an adult, it is sufficient for the neck attachment 106a to have a length approximately half the circumference of the adult's neck. The first portion configured to ensure that the device is inserted into a target part of the subject 104 may be in a form different from the neck attachment 106a and similarly, the dimensions of this first portion can be varied as long as they are large enough to allow the placement of sufficient sensors around the insertion point of the target part to obtain a certain level of tracking accuracy. The neck attachment 106a may also comprise a Velcro strap system to allow intuitive fitting of the neck attachment 106a to the subject's 104 neck.

The LEDs can also be arranged along a longer or shorter stretch of the neck attachment 106a, although usually, having the system 100 track the NG tube 102 up to 5 cm into the esophagus is sufficient to detect (and hence, aid the prevention of) the entry of the NG tube 102 into the trachea.

The body attachment 106b also need not be in the form shown in FIG. 3. Instead, the body attachment 106b can be in the form of a band. The body attachment 106b may or may not comprise flex sensors. It is preferable for both the neck attachment 106a and the body attachment 106b to include flex sensors but if it is desired to save costs by reducing the number of flex sensors, it is better if the flex sensors are omitted from the body attachment 106b rather than from the neck attachment 106a. This is because it is more important for the neck attachment 106a to achieve a high tracking accuracy as compared to the body attachment 106b. Further, the body attachment 106b can be of various sizes as long as the body attachment 106b is long enough to cover the distance from the chest to the stomach of a typical subject. The body attachment 106b may also be formed of various materials such as polyester, cotton or a mixture of these.

Also, although both the neck attachment 106a and body attachment 106b are used in the above embodiment, it is possible to use only one of these. The neck and body attachments 106a, 106b can be secured together while in use but this is not necessary.

The processing of the magnetic fields detected by the magnetic sensors also need not be performed in the manner as described above. Instead, the magnetic field can be modeled using other models such as magnetic dipole (MD) model and distributed multi-pole (DMP) model, although the accuracy of tracking the magnet when these models are used tend to be lower than that when the ANN model is used. In one example, the MD model (which is a magnetic field model that describes the magnetic source as a single dipole) is used as follows. As shown in FIG. 4, the vector pointing from the permanent magnet to the $i^{th}$ sensor can be defined as $P_i$ with a magnitude R. Using the MD model, the modeled magnetic field $B_{dm}$ induced by the permanent magnet at the $i^{th}$ sensor can be calculated as shown in Equation (4).

$$B_{dm} = \frac{\mu_r \mu_0 M}{4\pi} \left( \frac{3(H_0 \cdot P_i) P_i - R^3 \cdot H_0}{R^5} \right) \quad (4)$$

where $\mu_r$ is the relative permeability of the medium, $\mu_0$ is the magnetic permeability of free space (mT·mm/A), M is the constant strength of the dipole moment (A·mm²). The parameter M is a property of the specific magnet embedded in the device and can be obtained offline by calibration before use.

During the training process, an automated platform, such as a magnetic field mapping system or an industrial robot, can be used to move a specific magnet (which will later be used as the permanent magnet embedded in the device) to random positions and orientations, with reference to a magnetic sensor fixed at a particular position. Actual magnetic field measurements are obtained using the magnetic sensor as the specific magnet is moved to the random positions and orientations. The parameter M is determined by minimizing the differences between these actual magnetic field measurements and the modeled magnetic field measurements (calculated by Equation (4) with the random positions and orientations) using a least-square method. During training, it is preferable to move the specific magnet to as many positions and orientations as practically possible (with these positions and orientations being within the range of positions and orientations that the PM will be moved to during the actual use of the apparatus 106). This can help increase the accuracy of the trained MD model.

After the training process, Equation (4) is used to obtain modeled magnetic field measurements. These modeled magnetic field measurements are then used as $B_{mod\ ei}(P_s^i)$ in Equation (2) to determine the location $P_m=[x_m, y_m, z_m]^T$ and orientation $H_0=[u, v, w]^T$ of the permanent magnet (which is the specific magnet used during the training) embedded in the tip of the NG tube 102 as the NG tube 102 is inserted through a subject 104.

The embodiments of the present invention provide several advantages such as those described below.

The embodiments of the present invention provide real-time localization, live and accurate positional information of the NG tube 102. Thus, the insertion of the NG tube 102 need not be performed blindly and this places less reliance on the operator's skills and experience. Rather, the operator can continuously track and monitor in real-time the NG tube 102 insertion throughout the insertion process. For example, the visualizer 108 in the system 100 can help indicate the position of the NG tube 102 tip and an alarm can be sounded if any potential placement errors are about to occur. The operator can also or alternatively monitor the insertion using the LED indication on the wearable sensor network 106. Such real-time visual information can help ensure that the operator can react faster to any deviation during the NG intubation and can help provide to the operator more definitive confirmation on the placement of the NG tube 102 in the subject's 104 stomach. Thus, the NG intubation procedure is made safer as the risk of complications resulting from erroneous and improper placement of the NG tube 102 can be reduced.

The embodiments of the present invention also improve ease of use. Thus, NG intubation can be performed not only by experienced physicians but also physicians or other healthcare workers who are less experienced. In hospitals, this can help relieve the workload of the physicians so that they can focus on more complex procedures. In home care and rehabilitation facilities, nurses can be tasked to perform NG intubation with efficacy.

In addition, by embedding a small permanent magnet (PM) at the tip of the NG tube which is to be inserted into the subject 104 and using an optimized and intelligently distributed spatial sensor network in the form of the wearable sensor network 106 worn over the subject 104, the static magnetic fields produced by the PM can be robustly and accurately measured to track the NG tube 102 tip. Since the magnetic fields of a PM are passive fields, no auxiliary power is required. Also, with the embodiments of the present invention, the medical procedure and the device (e.g. NG tube 102) can remain fundamentally unmodified since the PM is merely embedded within the device. The embodiments of the present invention also help increase the cost effectiveness as even when the device (with the embedded PM) needs replacement, the external magnetic sensing units (e.g. wearable sensor network 106, visualizer 108) are reusable. The disposal process of the device can also remain the same.

The embodiments of the present invention also provide a radiation free and safe way of tracking the device. This is because no fluoroscopic confirmation is required and thus, the subject is not exposed to harmful X-ray radiation, which can be quite substantial over time considering that a NG tube for a patient has to be replaced every few months.

Embodiments of the invention thus provide an easy to use system that can not only improve safety of NG intubation but also reduce procedure time and discomfort to the subject 104. They can further help to reduce the overall cost for the subject 104.

Further, the wearable sensor network 106 contains compliant and flexible elements (such as the deformable parts "b" in the neck attachment 106a) that allow the wearable sensor network 106 to conform to the subject's 104 body.

Compared to products utilizing electromagnetic (EM) tracking, embodiments of the present invention have the advantages that:

They require less power since there is no need to energize an EM coil or create varying EM fields for detection, thus allowing the system to be moved around with less restriction;

They do not require changes in the insertion process of the device so there is no need to specially train the clinician to use the system in the embodiments of the present invention;

They are cost effective since only a small PM is embedded with the NG tube. Disposal of the NG tube with the PM is cheaper than disposal of a NG tube with expensive EM sensors attached to it;

They are more robust and reliable. Multiple sensors can be arranged around the patient and thus, redundancy against possible sensor failure is provided.

The invention claimed is:

1. A wearable sensor network for tracking a device having a magnet, the wearable sensor network comprising:
    at least one flexible element configured to conform to a subject;
    magnetic sensors arranged with the at least one flexible element to detect magnetic fields of the magnet as the device is inserted through the subject; and
    a plurality of indication elements located in positions corresponding to respective points along the subject;
    wherein the detected magnetic fields are processable to determine a position of the magnet to track the device as the device is inserted through the subject;
    wherein each indication element is configured to provide an indication when the magnet is within a predetermined range of the corresponding point along the subject.

2. A wearable sensor network according to claim 1, wherein the at least one flexible element comprises alternating parts of different rigidity.

3. A wearable sensor network according to claim 1, wherein the at least one flexible element is bendable to conform to the subject and the wearable sensor network further comprises flex sensors arranged with the at least one flexible element and configured to determine an extent the at least one flexible element bends.

4. A wearable sensor network according to claim 3, wherein the extent the at least one flexible element bends is used to determine positions of the magnetic sensors when the at least one flexible element is bent; and
wherein the position of the magnet is determined using the detected magnetic fields and the positions of the magnetic sensors when the at least one flexible element is bent.

5. A wearable sensor network according to claim 1, wherein the at least one flexible element comprises:
a first portion configured to ensure that the device is inserted into a target part of the subject; and
a second portion configured to ensure that the device is inserted through the subject to a target destination.

6. A wearable sensor network according to claim 1, further comprising FPGA localization electronics configured to process the detected magnetic fields to determine the position of the magnet.

7. A wearable sensor network according to claim 1, wherein the detected magnetic fields are processable to determine an orientation of the magnet.

8. A kit comprising:
a device comprising a magnet; and
a wearable sensor network for tracking the device comprising the magnet, the wearable sensor network comprising:
at least one flexible element configured to conform to a subject;
magnetic sensors arranged with the at least one flexible element to detect magnetic fields of the magnet as the device is inserted through the subject; and
a plurality of indication elements located in positions corresponding to respective points along the subject;
wherein the detected magnetic fields are processable to determine a position of the magnet to track the device as the device is inserted through the subject;
wherein each indication element is configured to provide an indication when the magnet is within a predetermined range of the corresponding point along the subject.

9. A wearable sensor network according to claim 1, wherein the indication elements comprise one or both of bi-coloured LEDs and alarms.

* * * * *